(12) United States Patent
Dryden, Jr. et al.

(10) Patent No.: US 10,932,762 B2
(45) Date of Patent: Mar. 2, 2021

(54) BIOPSY SAMPLING DEVICE

(71) Applicants: University of Louisville Research Foundation, Inc., Louisville, KY (US); Endoscopy Assist Devices, LLC, Crestwood, KY (US)

(72) Inventors: Gerald W. Dryden, Jr., Louisville, KY (US); Anthony Appling, Crestwood, KY (US)

(73) Assignees: University of Louisville Research Foundation, Inc., Louisville, KY (US); Endoscopy Assist Devices, LLC, Crestwood, KY (US)

( * ) Notice: Subject to any disclaimer, the term of this patent is extended or adjusted under 35 U.S.C. 154(b) by 195 days.

(21) Appl. No.: 15/754,533

(22) PCT Filed: Aug. 24, 2016

(86) PCT No.: PCT/US2016/048358
§ 371 (c)(1),
(2) Date: Feb. 22, 2018

(87) PCT Pub. No.: WO2017/035213
PCT Pub. Date: Mar. 2, 2017

(65) Prior Publication Data
US 2018/0271503 A1 Sep. 27, 2018

Related U.S. Application Data

(60) Provisional application No. 62/208,978, filed on Aug. 24, 2015.

(51) Int. Cl.
*A61B 5/00* (2006.01)
*A61B 10/02* (2006.01)
*A61B 10/04* (2006.01)

(52) U.S. Cl.
CPC .......... *A61B 10/0275* (2013.01); *A61B 10/04* (2013.01); *A61B 10/0283* (2013.01)

(58) Field of Classification Search
CPC ............ A61B 10/0266; A61B 10/0275; A61B 10/0283; A61B 10/04; A61B 2010/0208
See application file for complete search history.

(56) References Cited

U.S. PATENT DOCUMENTS

| 4,651,753 A | 3/1987 | Lifton |
| 5,183,052 A | 2/1993 | Terwilliger |

(Continued)

OTHER PUBLICATIONS

United States Patent and Trademark Office, International Search Report and Written Opinion issued in corresponding Application No. PCT/US16/48358, dated Nov. 15, 2016.

*Primary Examiner* — Max F Hindenburg
(74) *Attorney, Agent, or Firm* — Hamilton, Brook, Smith & Reynolds, P.C.

(57) ABSTRACT

A biopsy sampling device comprises a handle with a flexible cannula extending from the handle. The flexible cannula includes: an inner catheter, which defines an opening in a lateral wall surface thereof, and further defines a central lumen in fluid communication with the opening; an outer catheter positioned around and moveable relative to the inner catheter; and a cutting element positioned at a distal end of the outer catheter. The flexible cannula is configured such that a vacuum can be applied through the central lumen of the inner catheter to create a suction that draws a piece of tissue into the opening defined in the lateral wall surface of the inner catheter. The handle is configured to move the inner catheter relative to the outer catheter, such that the cutting element shears and severs the piece of tissue that has been drawn into the opening.

23 Claims, 6 Drawing Sheets

(56) References Cited

U.S. PATENT DOCUMENTS

| | | |
|---|---|---|
| 5,287,857 A | 2/1994 | Mann |
| 5,406,959 A | 4/1995 | Mann |
| 5,526,822 A | 6/1996 | Burbank et al. |
| 5,827,305 A | 10/1998 | Gordon |
| 6,027,458 A | 2/2000 | Janssens |
| 6,066,102 A | 5/2000 | Townsend et al. |
| 6,149,607 A | 11/2000 | Simpson et al. |
| 6,858,014 B2 | 2/2005 | Damarati |
| 7,794,409 B2 | 9/2010 | Damarati |
| 8,679,023 B2 | 3/2014 | Kobayashi |
| 8,986,334 B2 * | 3/2015 | Mark ............... A61B 17/32053 606/171 |
| 9,220,485 B2 * | 12/2015 | Parks ................ A61B 10/0045 |
| 9,247,929 B2 * | 2/2016 | Melsheimer ....... A61B 10/0275 |
| 9,845,021 B2 * | 12/2017 | Yang ...................... B60L 53/16 |
| 2002/0010416 A1 | 1/2002 | Uflacker |
| 2004/0116849 A1 | 6/2004 | Gardeski |
| 2008/0249553 A1 | 10/2008 | Gruber et al. |
| 2011/0190660 A1 | 8/2011 | Levy |
| 2011/0301496 A1 | 12/2011 | Lampropoulos et al. |
| 2012/0330186 A1 * | 12/2012 | Rhad .................. A61B 17/3403 600/567 |
| 2013/0150751 A1 * | 6/2013 | Fiebig ................ A61B 10/0275 600/566 |

* cited by examiner

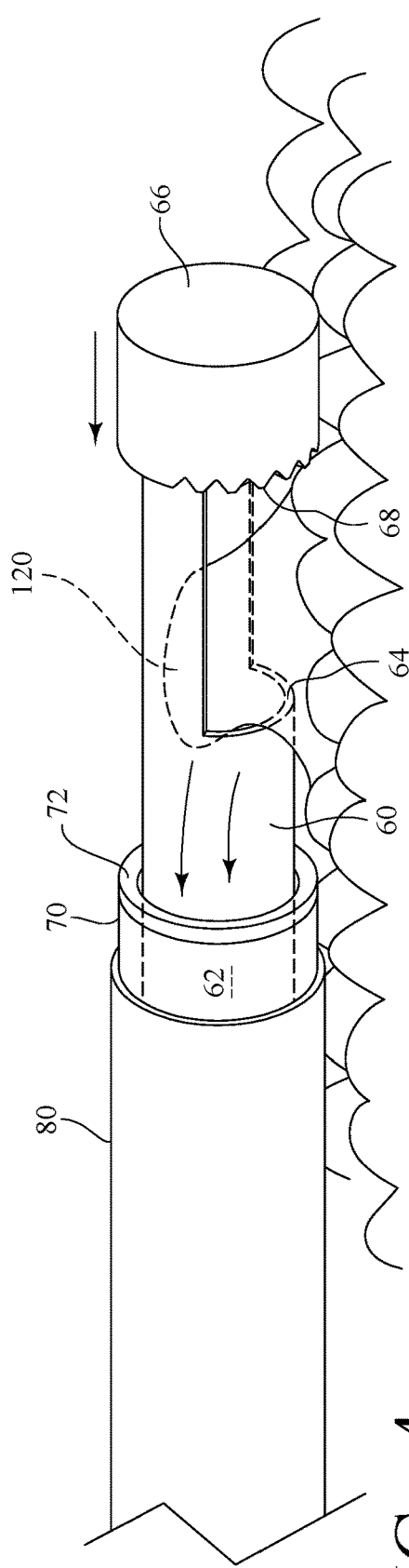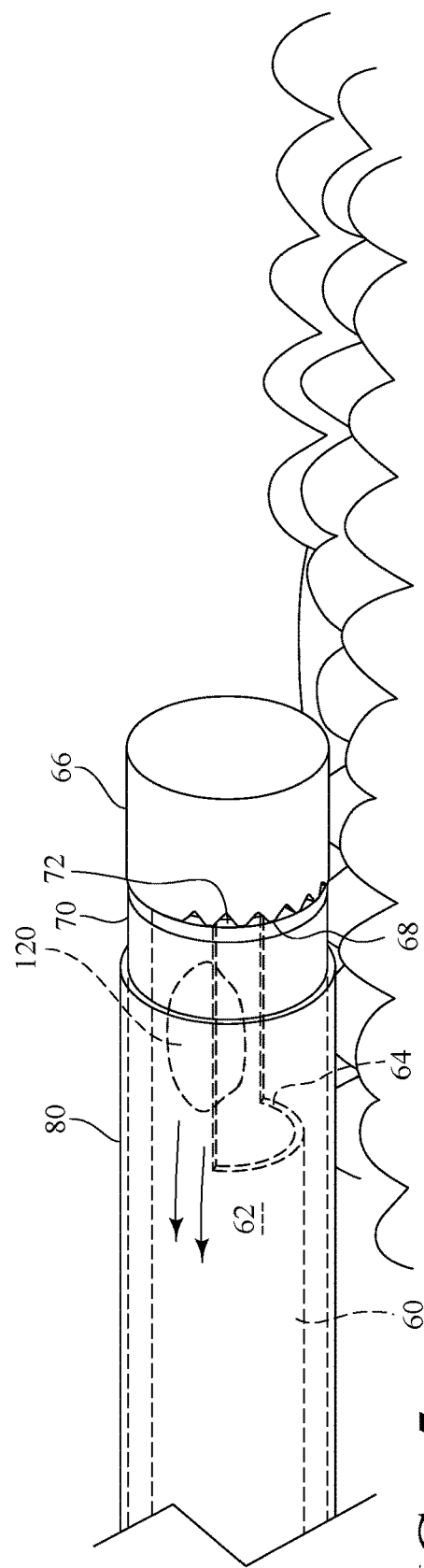

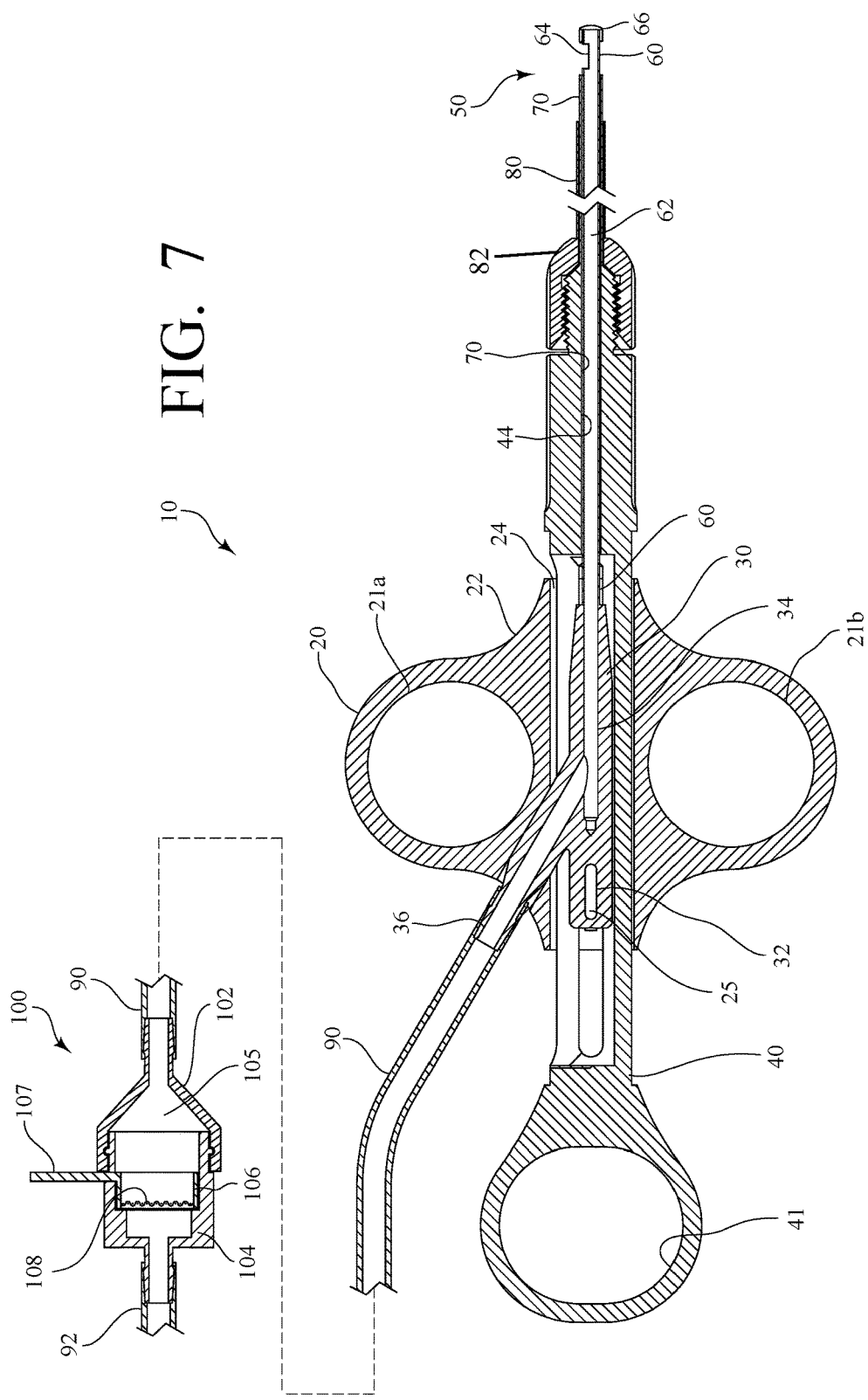

BIOPSY SAMPLING DEVICE

CROSS-REFERENCE TO RELATED APPLICATIONS

The present application claims priority to U.S. Patent Application Ser. No. 62/208,978 filed on Aug. 24, 2015, which is incorporated herein by reference.

BACKGROUND OF THE INVENTION

The present invention relates to a biopsy sampling device for obtaining one or more tissue samples, such as from the lining of the organ, an abnormal growth, or other abnormal finding. Such tissue samples are often taken as part of an endoscopic procedure, and many of the clinical indications for endoscopic biopsy require a multiple sample protocol. For example, in the case of chronic ulcerative colitis, an endoscopist may be required to obtain four separate biopsies at 10-cm intervals along the entire length of the colon, which could mean the harvest of 50-80 individual tissue samples. See Barkun, A., Liu, J., Carpenter, S., Chotiprasidhi, P., Chuttani, R., Ginsberg, G., Hussain, N., Silverman, W., Taitelabaum, G., Petersen, B. T. (2006). *Update on endoscopic tissue sampling devices. Gastrointestinal Endoscopy,* 63(6), 741-745. For another example, it has been estimated that at least 64 biopsies must be taken to attain ninety-five percent (95%) sensitivity for dysplasia. See Van Rijn, A. F., Fockens, P., Siersema, P. D., Oldenburg, B. (2009). *Adherence to surveillance guidelines for dysplasia and colorectal carcinoma in ulcerative and Crohn's colitis patients in the Netherlands. World Journal of Gastroenterology,* 15(2), 226-230.

The act of advancing the biopsy sampling device down the instrument channel of an endoscope and withdrawing the device to retrieve the sample accounts for the majority of time added to the overall time for the endoscopic procedure. The average pass takes one to two minutes or more, excluding the time it takes to extract the sample from the cups of the biopsy forceps. A stubborn sample may take several minutes to transfer to the formalin cup. Given that the average upper endoscopy may take five to seven minutes, endoscopic biopsy can double or even triple the total procedure time, depending on how many specimens must be obtained. Some disease states being monitored endoscopically require complex biopsy protocols, as in the case of performing surveillance biopsies for chronic colitis. Standard forceps are designed to take one sample at a time, while spiked forceps (which contain a spike in between the jaws) are capable of taking more than one biopsy. In order to add as little extra time to the total procedure time, researchers have evaluated the impact of taking more than two samples (i.e., with spiked forceps). See Fantin, A. C., Neuweiler, J., Binek, J. S., Suter, W. R., Meyenberger, C. (2001). *Diagnostic quality of biopsy specimens: Comparison between a conventional biopsy forceps and multibite forceps. Gastrointestinal Endoscopy,* 54(5), 600-604. The act of doubling the number of biopsies per pass does not appear to degrade the quality of the samples, but it does increase specimen loss, with up to thirty percent (30%) of samples going missing during the procedure. See Padda, S., Shah, I., Ramirez, F. C. (2003). *Adequacy of mucosal sampling with the "two-bite" forceps technique: a prospective, randomized, blinded study. Gastrointestinal Endoscopy,* 57(2), 170-173. Another source of missing biopsy specimens occurs due to the design of the rubber stopper on the instrument channel of most endoscopes. The rubber stopper prevents air or gastrointestinal contents from leaking out of the scope during the procedure, but the tight seal also may strip tissue from the biopsy forceps. Tissue loss can be quite unfortunate, since some lesions needing histologic analysis may be lost in their entirety, as the size of the lesion was only as large as one pinch of the biopsy forceps. This situation can also apply to the removal of small polyps by biopsy forceps. If the tissue falls off the spike, it may no longer be available for analysis. This prevents appropriate recommendations for follow-up procedures from being made. Additionally, recent studies demonstrated that twenty percent (20%) of polypectomies performed with cold biopsy forceps resulted in an incomplete polypectomy. See Lee, C. K., Shim, J-J., Jang, J. Y. (2013). *Cold Snare Polypectomy vs. Cold Forceps Polypectomy Using Double-Biopsy Technique for Removal of Diminutive Colorectal Polyps: A Prospective Randomized Study. The American Journal of Gastroenterology,* 108(10), 1593-1600. Incomplete polypectomy allows continued growth of the polyp during the interval period between colonoscopies, which can be a cause of interval colon cancers. See Pohl, H., Srivastava, A., Bensen, S. P., Anderson, P., Rothstein, R. I., Gordon, S. R., Levy, L. C., Toor, A., Mackenzie, T. A., Rosch, T., Robertson, D. J. (2013). *Incomplete polyp resection during colonoscopy-results of the complete adenoma resection (CARE) study. Gastroenterology,* 144(1), 74-80.

Thus, there remains a need for a biopsy sampling device that improves the efficiency of obtaining tissue samples, especially when multiple tissue samples are needed.

SUMMARY OF THE INVENTION

The present invention is a biopsy sampling device for obtaining one or more tissue samples, such as from the lining of the organ, an abnormal growth, or other abnormal finding, and then transporting those tissue samples out of the body to a collection device. The biopsy sampling device of the present invention allows for multiple sampling of the lining of the organ, an abnormal growth, or other abnormal finding without removal of the device from the body.

An exemplary biopsy sampling device made in accordance with the present invention includes a handle, along with a flexible cannula that extends from the handle and has a sufficient length to be advanced from outside of the body of the patient, preferably through an instrument channel of an endoscope or through a laparoscopic port, while the handle remains outside of the body.

The flexible cannula is not a unitary member, but rather is comprised of multiple elements in a coaxial arrangement. In some embodiments, the flexible cannula comprises: an inner catheter; an outer catheter that is positioned around and moveable relative to the inner catheter; and a sheath that is positioned around the outer catheter.

An opening is defined in a lateral wall surface of the inner catheter near its distal end. This opening is in fluid communication with a central lumen (that extends the length of the inner catheter, such that there is a continuous airway from the opening at the distal end of the biopsy sampling device through the central lumen of the inner catheter. Furthermore, in some embodiments, there is a cap positioned at the distal end of the inner catheter that includes integral teeth in the vicinity of the opening. Finally, the biopsy sampling device also includes a cutting element that is positioned at the distal end of the outer catheter, which may be in the form of a ring that circumscribes the inner catheter.

In use, the biopsy sampling device is positioned for retrieving a tissue sample. Thus, in most cases, the flexible cannula would be advanced through an instrument channel of an endoscope or through a laparoscopic port. The opening defined in the lateral wall surface of the inner catheter is then positioned near a tissue of interest, such as the lining of the organ, an abnormal growth, or other abnormal finding. A vacuum is then applied through the central lumen of the inner catheter, which creates a suction that draws a piece of tissue into the opening. The inner catheter is then moved and withdrawn relative to the outer catheter, with the cutting element then shearing and severing the piece of tissue that has been drawn into the opening defined in the lateral wall surface of the inner catheter. Continued application of the vacuum draws the severed piece of tissue through the central lumen of the inner catheter, where it can be received in a collection device.

As a result of such a construction, the exemplary biopsy sampling device is particularly well-suited for taking multiple tissue samples. Specifically, once a tissue sample has been taken, the vacuum can be turned off, and the flexible cannula can then be moved along the lining of the organ, an abnormal growth, or other abnormal finding to another position, where another tissue sample can be taken, and so on. Thus, sampling can be continued indefinitely without removing the flexible cannula from the body.

DESCRIPTION OF THE DRAWINGS

FIG. 4 is a view similar to FIG. 2, wherein an inner catheter of the biopsy sampling device is withdrawn relative to the outer catheter, with the cutting element then shearing and severing the piece of tissue that has been drawn into the opening defined by the inner catheter.

FIG. 5 is a view similar to FIG. 2, wherein the piece of tissue has been completely severed;

FIG. 7 is a sectional view of the exemplary biopsy sampling device of FIG. 1.

DETAILED DESCRIPTION OF THE INVENTION

The present invention is a biopsy sampling device for obtaining one or more tissue samples, such as from the lining of the organ, an abnormal growth, or other abnormal finding, and then transporting those tissue samples out of the body to a collection device. The biopsy sampling device of the present invention allows for multiple sampling of the lining of the organ, an abnormal growth, or other abnormal finding without removal of the device from the body. In practice, such a biopsy sampling device may be useful for various types of procedures, including, but not limited to: gastrointestinal endoscopic procedures, such as a colonoscopy for surveillance of dysplasia associated with long-term colitis; upper gastrointestinal endoscopic procedures, such as an esophagogastroduodenoscopy for surveillance of dysplasia associated with Barrett's intestinal metaplasia; and general endoscopic biopsies. Additionally, such a biopsy sampling device may be useful in examinations of the oropharynx, sinuses, bronchial tubes/lungs, biliary tree, bladder, or intra-abdominal lesions through a laparoscopic port.

Figure 1:
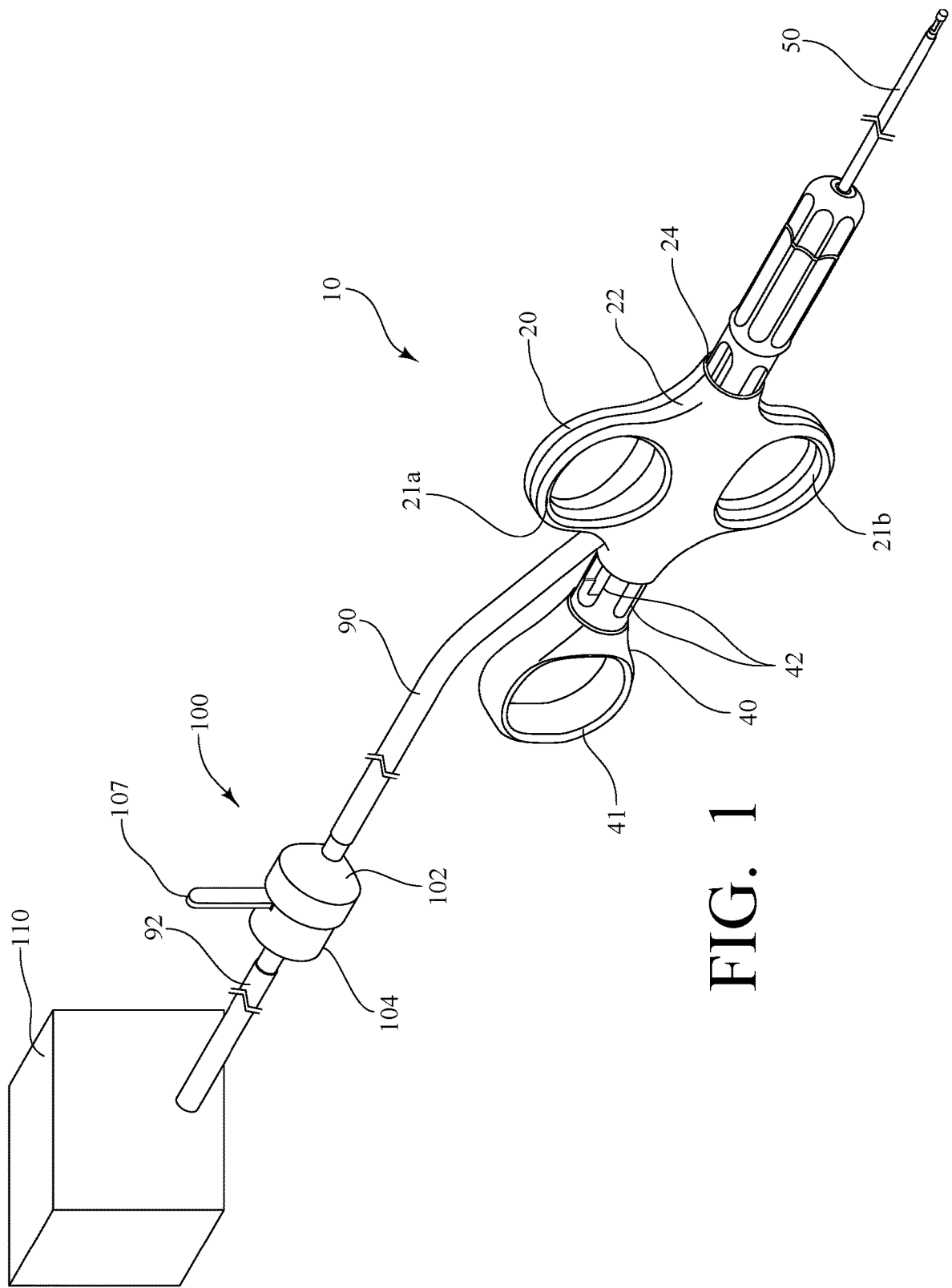
FIG. 1 is a perspective view of an exemplary biopsy sampling device made in accordance with the present invention.
Figure 2:
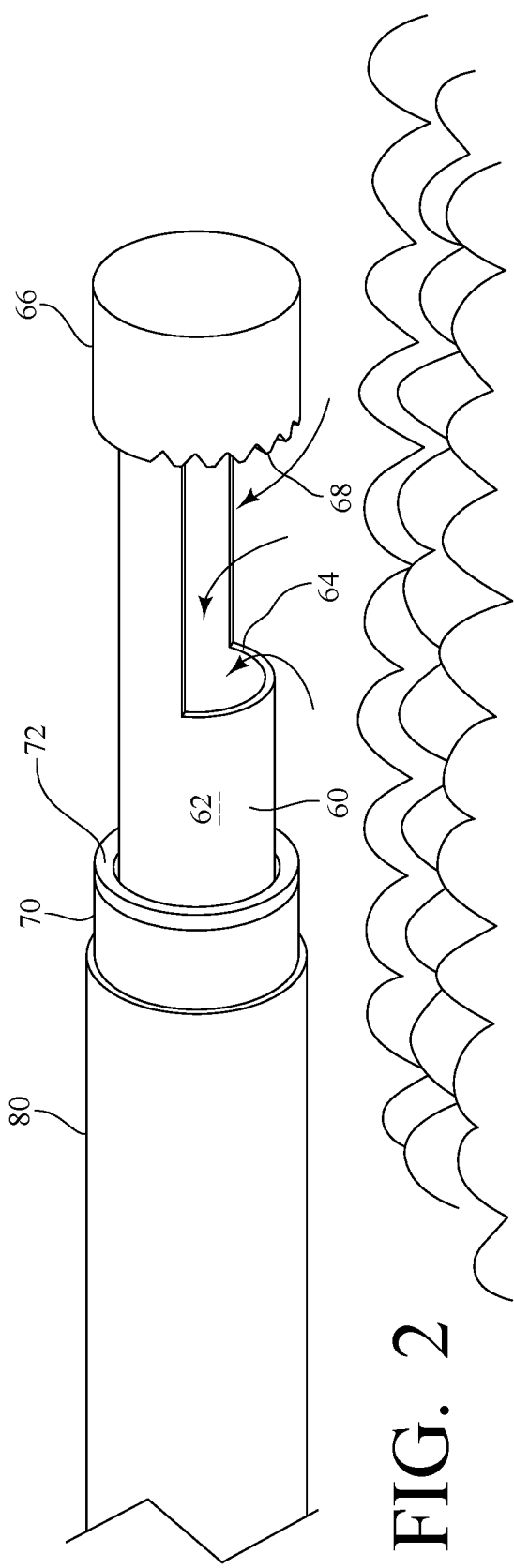
FIG. 2 is a view of the distal end of the exemplary biopsy sampling device of FIG. 1 as positioned near a tissue of interest.

Referring now to FIG. 1, an exemplary biopsy sampling device 10 made in accordance with the present invention includes a handle 20, along with a flexible cannula 50 that extends from the handle 20. Although the flexible cannula 50 appears to be relatively short in FIG. 1, in practice, this flexible cannula 50 would have a sufficient length to be advanced from outside of the body of the patient, preferably through an instrument channel of an endoscope or through a laparoscopic port, while the handle 20 remains outside of the body, as will be further discussed below. A first tube 90 extends from the handle 20, but in the opposite direction, where it is in fluid communication with a collection device 100. A second tube 92 then extends from the collection device 100 and places the collection device 100 in fluid communication with a vacuum source 110, as will also be further discussed below.

Referring now to FIGS. 2-6, the flexible cannula 50 is not a unitary member, but rather is comprised of multiple elements in a coaxial arrangement. Specifically, in this exemplary embodiment, the flexible cannula 50 comprises: an inner catheter 60; an outer catheter 70 that is positioned around and moveable relative to the inner catheter 60; and a sheath 80 that is positioned around the outer catheter 70. Of course, each of these catheters 60, 70 and the sheath 80 are also flexible, and suitable materials for the manufacture of these catheters 60, 70 and the sheath 80 include, but are not limited to, polyether ether ketone (PEEK), polyimide, polyethylene, and other similar thermoplastics. Furthermore, polytetrafluoroethylene (PTFE) or a similar additive can be incorporated into the material for one or both of the catheters 60, 70 in order to reduce friction, the importance of which will be further discussed below. Alternatively, a coating could be applied to the surfaces of one or both of the catheters 60, 70 to decrease friction, such as MDX4-4159, a medical-grade lubricant manufactured and distributed by Dow Corning Corporation of Auburn, Mich.

Figure 2A:
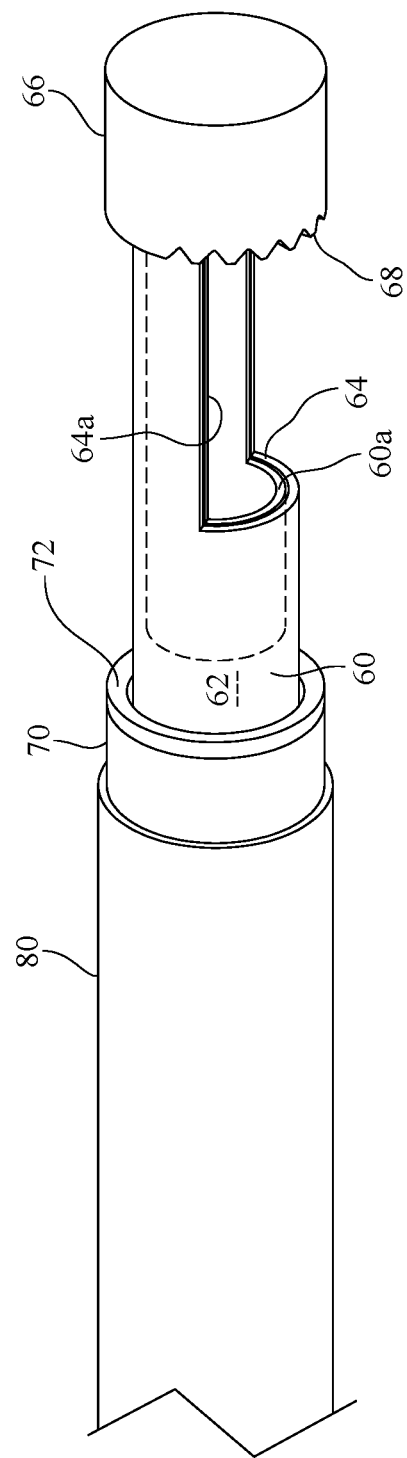
FIG. 2A is a view of an alternate biopsy sampling device made in accordance with the present invention in which the inner catheter includes an insert at its distal end.

Referring still to FIGS. 2-6, an opening 64 is defined in a lateral wall surface of the inner catheter 60 near its distal end. In this regard, although not shown in the Figures, in some embodiments, the distal end of the inner catheter 60 may be manufactured from an alternate material to create a more rigid and stable structure in the vicinity of the opening 64 for the subsequent shearing and severing action (as will be further discussed below). Alternatively, in some embodiments, and as shown in FIG. 2A, the inner catheter 60 is provided with an insert 60a at its distal end to provide the desired rigidity and stability in the vicinity of the opening 64. For example, such an insert 60a may be formed from a segment of hypodermic tube (or hypotube), which is commonly manufactured from nitinol (nickel titanium alloy) or stainless steel. Of course, such an insert would include a corresponding opening 64a in its wall surface that is in registry with the opening 64 defined in the lateral wall surface of the inner catheter 60.

In any event, the opening 64 is in fluid communication with a central lumen (or channel) 62 that extends the length of the inner catheter 60, such that there is a continuous airway from the opening 64 at the distal end of the biopsy sampling device 10 through the central lumen 62 of the inner catheter 60. Furthermore, there is a cap 66 positioned at the distal end of the inner catheter 60 that, in this exemplary embodiment, includes integral teeth 68 in the vicinity of the opening 64, the importance of which will be further discussed below. Finally, the biopsy sampling device 10 also includes a cutting element 72, which may be manufactured from, for example, nitinol (nickel titanium alloy), tempered stainless steel, or other suitable metal. As shown, in this exemplary embodiment, the cutting element 72 is positioned at the distal end of the outer catheter 70, and, in this exemplary embodiment, is in the form of a ring that circumscribes the inner catheter 60.

Referring still to FIGS. 2-6, in use, the biopsy sampling device 10 is positioned for retrieving a tissue sample. Thus, in most cases, the flexible cannula 50 would be advanced through an instrument channel of an endoscope or through a laparoscopic port, and thus, the flexible cannula 50 would preferably have an outer diameter of less than approximately 2.6 mm. The opening 64 defined in the lateral wall surface of the inner catheter 60 is then positioned near a tissue of interest, such as the lining of the organ, an abnormal growth, or other abnormal finding. In this regard, it is contemplated that the inner catheter 60 can be rotated, at least to some extent, relative to the outer catheter 70 to properly position the opening 64.

Figure 3:
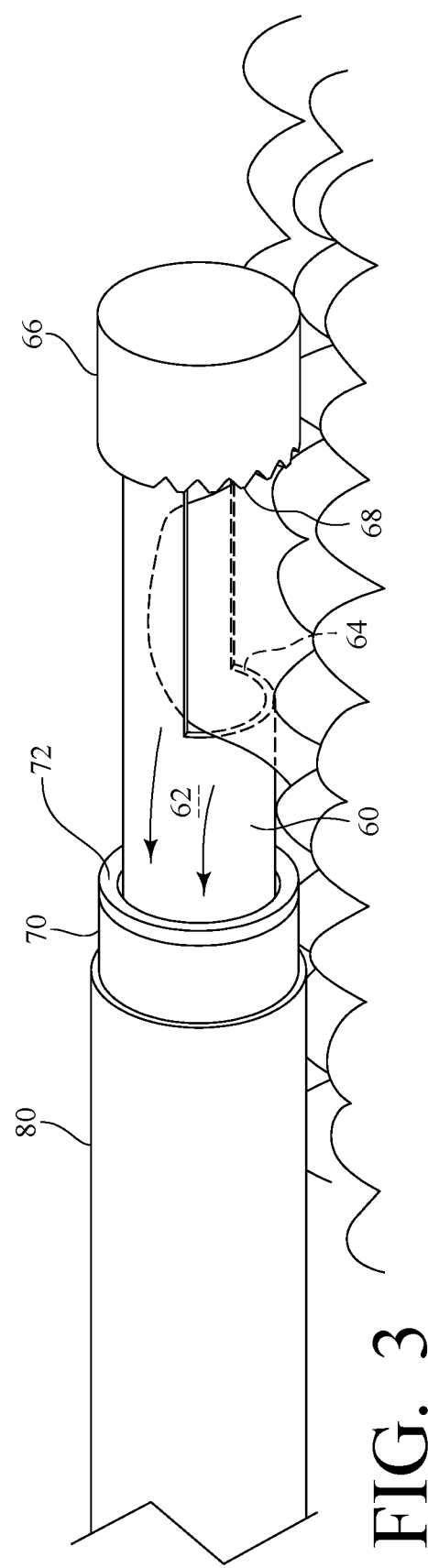
FIG. 3 is a view similar to FIG. 2, wherein a vacuum has been applied to draw a piece of tissue into an opening defined by an inner catheter of the biopsy sampling device.

Referring still to FIGS. 2-6, a vacuum is then applied through the central lumen 62 of the inner catheter 60. (The application of the vacuum will be further discussed below.) Such a vacuum creates a suction that draws a piece of tissue 120 into the opening 64, as best shown in FIG. 3. The inner catheter 60 is then moved and withdrawn relative to the outer catheter 70 (as will be further discussed below), with the cutting element 72 then shearing and severing the piece of tissue 120 that has been drawn into the opening 64 defined in the lateral wall surface of the inner catheter 60, as best shown in FIGS. 4 and 5. In this regard, such movement has no impact on the application of the vacuum as the opening 64 is effectively closed. In this exemplary embodiment and as shown in FIG. 5, the cap 66 acts as a stop and limits movement of the inner catheter 60 relative to the inner outer catheter 70. Furthermore, in this exemplary embodiment, the integral teeth 68 aid in grasping, shearing, and severing the piece of tissue 120. In other words, tissue is effectively grasped and gathered up between the cutting element 72 and the teeth 68 of the cap 66 as the inner catheter 60 moves relative to the outer catheter 70. Finally, although not indicated in the Figures, in some embodiments, the cap 66 may be provided with a pointed tip (or one or more spikes) or otherwise configured to engage tissue and position the flexible cannula 50.

Figure 6:
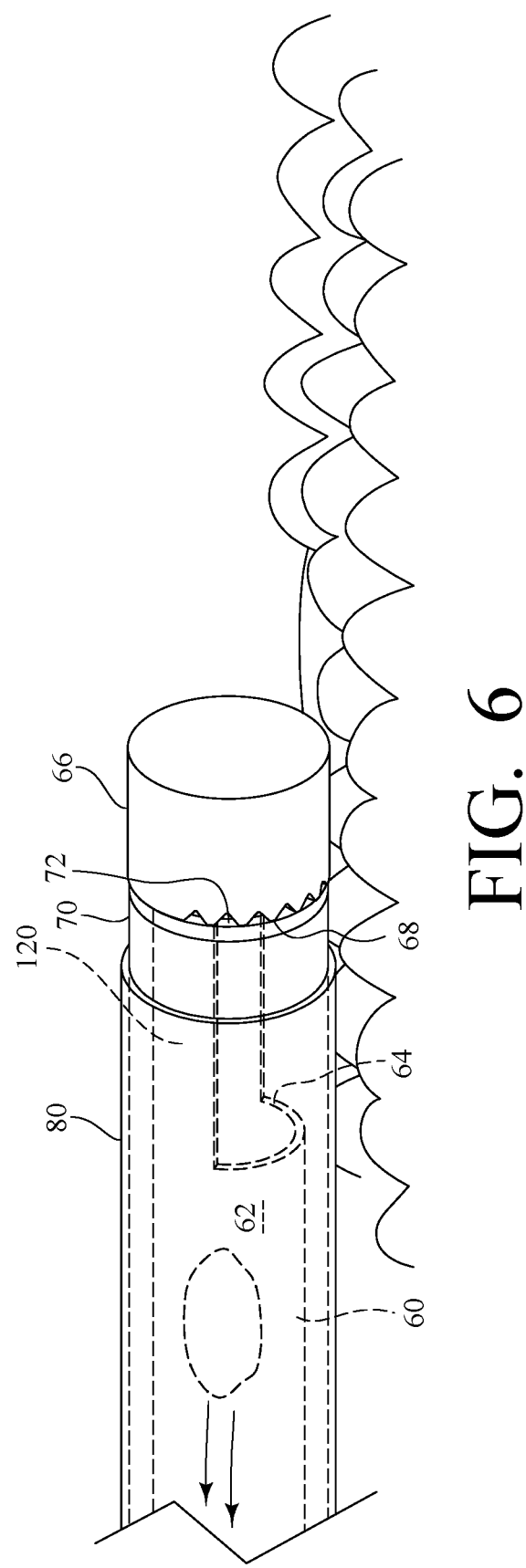
FIG. 6 is a view similar to FIG. 2, wherein the piece of tissue that has been completely severed is drawn back through the central lumen of the inner catheter by the continued application of the vacuum.

Of course, and as best shown in FIG. 6, continued application of the vacuum draws the severed piece of tissue 120 through the central lumen 62 of the inner catheter 60, where it can be received in the collection device 100, as will be further discussed below.

As a result of such a construction, the exemplary biopsy sampling device 10 is particularly well-suited for taking multiple tissue samples. Specifically, once a tissue sample has been taken, the vacuum can be turned off, and the flexible cannula 50 can then be moved along the lining of the organ, an abnormal growth, or other abnormal finding to another position, where another tissue sample can be taken, and so on. Thus, sampling can be continued indefinitely without removing the flexible cannula 50 from the body.

Referring now to the sectional view of FIG. 7, the handle 20 of the exemplary biopsy sampling device 10 includes a central portion 22 which defines a passageway 24. A connecting element 30 is received in this passageway 24 and is in a fixed position relative to the central portion 22 of the handle 20. Specifically, in this exemplary embodiment, the central portion 22 of the handle 20 includes at least one integral tab 25 that engages a corresponding slot 32 defined by the connecting element 30, thus fixing the position of the connecting element 30 relative to the central portion 22 of the handle 20.

Referring still to FIG. 7, the connecting element 30 itself then defines a central channel 34, and a proximal end of the inner catheter 60 is received and secured in this central channel 34. The connecting element 30 further defines a secondary channel 36. As shown, a first end of the secondary channel 36 is placed in fluid communication with the central lumen 62 of the inner catheter 60, in this case, via an opening defined through the side wall of the inner catheter 60 near its proximal end. Thus, a continuous airway is formed through the central lumen 62 of the inner catheter 60 and the secondary channel 36 defined by the connecting element 30. A second end of the secondary channel 36 defined by the connecting element 30 is then connected to the first tube 90.

Referring still to FIG. 7, the first tube 90 is then connected to the collection device 100. The collection device 100 is intended to capture tissue samples, i.e., the pieces of tissue that are sheared and served by the biopsy sampling device 10. In this exemplary embodiment, the collection device 100 includes an upper section 102, a lower section 104 connected to the upper section 102, and an intermediate tray 106 with a screen 108 defined in or integrated into its bottom surface. The upper section 102 and the lower section 104 preferably snap together, are screwed together, or are otherwise connected to create an internal cavity 105, with the intermediate tray 106 positioned in this internal cavity 105.

Referring still to FIG. 7, the first tube 90 is connected to the upper section 102, placing the internal cavity 105 in fluid communication with the secondary channel 36 defined by the connecting element 30 via the first tube 90. The second tube 92 is then connected to the lower section 104 at one end and the vacuum source 110 at the opposite end. As result, the above-described continuous airway formed through the central lumen 62 of the inner catheter 60 and the secondary channel 36 defined by the connecting element 30 is extended through the collection device 100 (via the first tube 90) and to the vacuum source 110 (via the second tube 92).

As a result, activation of the vacuum source 110, which is located outside of the body, creates the necessary suction through the continuous airway to draw a piece of tissue 120 into the opening 64 defined in the lateral wall surface of the inner catheter 60 when it is positioned within the body for retrieving a tissue sample. As mentioned above, continued application of the vacuum draws the severed piece of tissue 120 through the central lumen 62 of the inner catheter 60. It is then passed through the secondary channel 36 defined by the connecting element 30 within the handle 20, and exits the secondary channel 36 via the first tube 90. The severed piece of tissue 120 is then drawn into the collection device 100 and captured by the screen 108 of the intermediate tray 106. Once the vacuum source 110 has been turned off, the severed piece of tissue 120 can be readily accessed for subsequent histologic analysis by disassembling the upper section 102 of the collection device 100 from the lower section 104, and then removing the intermediate tray 106, which includes a handle 107 to facilitate such removal. However, the flexible catheter 50 does not need to be removed from the body (i.e., from the instrument channel of the endoscope or from the laparoscopic port) to collect the severed piece of tissue and can remain in place to collect additional samples.

Although one exemplary collection device 100 is illustrated in FIGS. 1 and 7 and described above, it is contemplated that various collection devices could be used in the biopsy sampling device 10 without departing from the spirit and scope of the present invention.

Referring again to FIGS. 1 and 7, the handle 20 also facilitates the movement of the inner catheter 60 relative to the outer catheter 70, and thus, facilitates the shearing and severing action. In this regard, the handle 20 further includes a plunger 40, which extends through the passageway 24 defined by the central portion 22 of the handle 20. This plunger 40 is configured for relative movement with respect to the central portion 22 of the handle 20. In this regard, as perhaps best shown in FIG. 1, portions of the circumferential wall of the plunger 40 include longitudinal slots 42, such that the plunger 40 can effectively move forward and rearward with respect to the central portion 22 of the handle 20 without interference with other internal components, such as the above-described tab 25 or the portion of the connecting element 30 that defines the secondary channel 36. In other words, and as best shown in FIG. 7, the tab 25 passes through one of the longitudinal slots 42, and the portion of the connecting element 30 that defines the secondary channel 36 similarly passes through one of the longitudinal slots 42, so that the plunger 40 can effectively move forward and rearward with respect to the central portion 22 of the handle 20, at least for a limited distance, without interference.

Furthermore, and referring still to FIGS. 1 and 7, in this exemplary embodiment, the plunger 40 defines an opening 41 at a first end for accommodating a thumb (or other finger) of a user, while the central portion 22 of the handle 20 defines similar lateral openings 21a, 21b to accommodate the forefinger and middle finger (or other fingers) of the user. Thus, with one hand, a user can withdraw the central portion 22 (i.e., move it rearward) relative to the plunger 40, while the plunger 40 remains in a static position. Alternatively, the user can apply pressure to the plunger 40 and advance the plunger (i.e., move it forward) relative to the central portion 22 of the handle 20. In either case, there is relative movement between the central portion 22 of the handle and the plunger 40.

Referring still to FIGS. 1 and 7, the plunger 40 is operably connected to the outer catheter 70, while the central portion 22 of the handle 20 is operably connected to the inner catheter 60, such that movement of the central portion 22 of the handle 20 relative to the plunger 40 (or vice versa) causes a corresponding movement of the inner catheter 60 relative to the outer catheter 70. In this exemplary embodiment, and as shown in FIG. 7, the plunger 40 defines a central channel 44, and a proximal end of the outer catheter 70 is received and secured in this central channel 44.

Finally, as mentioned above, in this exemplary embodiment, a sheath 80 is positioned around the outer catheter 70 and completes the assembly of the flexible cannula 50. As shown in FIGS. 1 and 7, the sheath 80 is fixed to and extends from a cap 82, which, in turn, engages a distal end of the plunger 40. Specifically, in this exemplary embodiment, the distal end of the plunger 40 includes external threads, which mate with corresponding internal threads of the cap 82, thus connecting the cap 82 and the sheath 80 to the plunger 40.

As a further refinement, although not shown in the Figures, it is contemplated that the cutting element 72, which is preferably made of metal, could be electrified with monopolar current to produce a cauterizing effect while the tissue is being biopsied, while the other components in the vicinity are insulated against cautery leak. The cautery could be applied intermittently during the biopsy process to reduce bleeding complications induced by the biopsy process or facilitate removal of the tissue.

One of ordinary skill in the art will recognize that additional embodiments and implementations are also possible without departing from the teachings of the present invention. This detailed description, and particularly the specific details of the exemplary embodiments disclosed therein, is given primarily for clarity of understanding, and no unnecessary limitations are to be understood therefrom, for modifications will become obvious to those skilled in the art upon reading this disclosure and may be made without departing from the spirit or scope of the present invention.

What is claimed is:

1. A biopsy sampling device, comprising:
a handle; and
a flexible cannula extending from the handle, the flexible cannula including (a) an inner catheter, wherein the inner catheter defines an opening in a lateral wall surface thereof, and
wherein the inner catheter defines a central lumen in fluid communication with the opening, (b) an outer catheter positioned around and moveable relative to the inner catheter, and (c) a cutting element positioned at a distal end of the outer catheter;
wherein the flexible cannula is configured such that a vacuum can be applied through the central lumen of the inner catheter to create a suction that draws a piece of tissue into the opening defined in the lateral wall surface of the inner catheter; and
wherein the handle is configured to cause relative movement of the inner catheter and the outer catheter, such that the cutting element shears and severs the piece of tissue that has been drawn into the opening defined in the lateral wall surface of the inner catheter as the opening is translated to a position within the outer catheter, thereby fixing the piece of tissue in position with respect to the central lumen during shearing and severing and limiting application of the vacuum to the piece of tissue.

2. The biopsy sampling device as recited in claim 1, wherein the cutting element is in the form of a ring that circumscribes the inner catheter.

3. The biopsy sampling device as recited in claim 1, wherein the inner catheter includes an insert at its distal end, with the insert including a corresponding opening in its wall surface that is in registry with the opening defined in the lateral wall surface of the inner catheter.

4. The biopsy sampling device as recited in claim 1, and further comprising a collection device in fluid communication with the central lumen of the inner catheter.

5. The biopsy sampling device as recited in claim 4, wherein the vacuum is applied through the collection device and then through the central lumen of the inner catheter.

6. The biopsy sampling device as recited in claim 5, wherein a continuous airway is formed through the central lumen of the inner catheter, through the handle, and through the collection device to a vacuum source.

7. The biopsy sampling device as recited in claim 1, and wherein the flexible cannula further comprises a sheath that is positioned around the outer catheter.

8. The biopsy sampling device as recited in claim 1, and further comprising a cap positioned at a distal end of the inner catheter that acts as a stop and limits movement of the inner catheter relative to the outer catheter.

9. The biopsy sampling device as recited in claim 8, wherein the cap includes teeth to aid in grasping, shearing, and severing the piece of tissue.

10. The biopsy sampling device as recited in claim 6, wherein the handle includes:
   a central portion which defines a passageway;
   a connecting element received in the passageway in a fixed position relative to the central portion, with a proximal end of the inner catheter received and secured in a central channel defined by the connecting element; and
   a plunger which extends through the passageway defined by the central portion and is configured for movement relative to the central portion, with a proximal end of the outer catheter received in and secured by the plunger, such that movement of the central portion relative to the plunger causes a corresponding movement of the inner catheter relative to the outer catheter.

11. The biopsy sampling device as recited in claim 10, wherein the connecting element further defines a secondary channel, with a first end of the secondary channel being placed in fluid communication with the central lumen of the inner catheter, thus forming the continuous airway through the handle between the central lumen of the inner catheter and the collection device.

12. The biopsy sampling device as recited in claim 4, wherein the collection device includes:
   an upper section;
   a lower section connected to the upper section, thus creating an internal cavity; and
   an intermediate tray positioned in the internal cavity and having a screen for capturing the piece of tissue.

13. A biopsy sampling device, comprising:
   a flexible inner catheter, wherein the inner catheter defines an opening in a lateral wall surface thereof, and wherein the inner catheter defines a central lumen in fluid communication with the opening;
   a flexible outer catheter positioned around and moveable relative to the inner catheter; and
   a cutting element positioned at a distal end of the outer catheter;
   wherein, in use, a vacuum is applied through the central lumen of the inner catheter to create a suction that draws a piece of tissue into the opening defined in the lateral wall surface of the inner catheter;
   wherein, in use, the inner catheter and the outer catheter are relatively moved, such that the cutting element shears and severs the piece of tissue that has been drawn into the opening defined in the lateral wall surface of the inner catheter as the opening is translated to a position within the outer catheter, thereby fixing the piece of tissue in position with respect to the central lumen during shearing and severing and limiting application of the vacuum to the piece of tissue; and
   wherein, in use, continued application of the vacuum draws the piece of tissue though the central lumen of the inner catheter.

14. The biopsy sampling device as recited in claim 13, wherein the cutting element is in the form of a ring that circumscribes the inner catheter.

15. The biopsy sampling device as recited in claim 13, wherein the inner catheter includes an insert at its distal end, with the insert including a corresponding opening in its wall surface that is in registry with the opening defined in the lateral wall surface of the inner catheter.

16. The biopsy sampling device as recited in claim 13, and further comprising a collection device in fluid communication with the central lumen of the inner catheter.

17. The biopsy sampling device as recited in claim 16, wherein the vacuum is applied through the collection device and then through the central lumen of the inner catheter.

18. The biopsy sampling device as recited in claim 13, and further comprising a sheath that is positioned around the outer catheter.

19. The biopsy sampling device as recited in claim 13, and further comprising a cap positioned at a distal end of the inner catheter that acts as a stop and limits movement of the inner catheter relative to the outer catheter.

20. The biopsy sampling device as recited in claim 19, wherein the cap includes teeth to aid in grasping, shearing, and severing the piece of tissue.

21. The biopsy sampling device as recited in claim 13, and further comprising a handle which includes:
   a central portion, wherein a proximal end of the inner catheter is secured in a fixed position relative to the central portion; and
   a plunger which extends through a passageway defined by the central portion and is configured for movement relative to the central portion, with a proximal end of the outer catheter received in and secured by the plunger, such that movement of the plunger relative to the central portion causes a corresponding movement of the outer catheter relative to the inner catheter.

22. A method for taking a biopsy, comprising:
   providing a biopsy sampling device having (a) an inner catheter, wherein the inner catheter defines an opening in a lateral wall surface thereof, and wherein the inner catheter defines a central lumen in fluid communication with the opening, (b) an outer catheter positioned around and moveable relative to the inner catheter, and (c) a cutting element positioned at a distal end of the outer catheter;
   advancing the outer catheter and the inner catheter of the biopsy sampling device through an instrument channel of an endoscope or through a laparoscopic port;
   positioning the opening defined in the lateral wall surface of the inner catheter near a tissue of interest;
   applying a vacuum at a proximal end of the inner catheter through the central lumen of the inner catheter to create a suction that draws a piece of tissue into the opening defined in the lateral wall surface of the inner catheter; and
   relatively moving the inner catheter and the outer catheter, such that the cutting element shears and severs the piece of tissue that has been drawn into the opening defined in the lateral wall surface of the inner catheter as the opening is translated to a position within the outer catheter, thereby fixing the piece of tissue in position with respect to the central lumen during shearing and severing and limiting application of the vacuum to the piece of tissue.

23. The method for taking a biopsy as recited in claim 22, and further comprising positioning a collection device in fluid communication with the central lumen of the inner catheter to capture the piece of tissue.

\* \* \* \* \*